(12) United States Patent
Wu et al.

(10) Patent No.: US 10,100,298 B1
(45) Date of Patent: Oct. 16, 2018

(54) MALTOOLIGOSYL TREHALOSE SYNTHASE MUTANT AND ITS APPLICATION

(71) Applicant: Jiangnan University, Wuxi (CN)

(72) Inventors: Jing Wu, Wuxi (CN); Lingqia Su, Wuxi (CN); Kailin Yao, Wuxi (CN)

(73) Assignee: Jiangnan University, Wuxi, Jiangsu Province (CN)

( * ) Notice: Subject to any disclaimer, the term of this patent is extended or adjusted under 35 U.S.C. 154(b) by 0 days.

(21) Appl. No.: 15/820,487

(22) Filed: Nov. 22, 2017

(30) Foreign Application Priority Data

Sep. 13, 2017 (CN) .......................... 2017 1 0822065

(51) Int. Cl.
*C12N 9/10* (2006.01)
*C12N 9/90* (2006.01)
*C12P 19/12* (2006.01)

(52) U.S. Cl.
CPC ................ *C12N 9/90* (2013.01); *C12P 19/12* (2013.01); *C12Y 504/99015* (2013.01)

(58) Field of Classification Search
CPC .................................................... C12N 9/1051
See application file for complete search history.

(56) References Cited

U.S. PATENT DOCUMENTS

| 5,922,578 | A | * | 7/1999 | Maruta | ................... | C12P 19/12 |
| | | | | | | 435/101 |
| 5,976,856 | A | * | 11/1999 | Maruta | ................... | C12P 19/12 |
| | | | | | | 435/101 |

\* cited by examiner

*Primary Examiner* — Maryam Monshipouri
(74) *Attorney, Agent, or Firm* — IPro, PLLC; Na Xu

(57) ABSTRACT

The present invention relates to the field of genetic engineering and enzyme engineering, and more particularly relates to a maltooligosyl trehalose synthase mutant and its application. The present invention provides a series of maltooligosyl trehalose synthase mutants with improved enzyme activity.

3 Claims, No Drawings

Specification includes a Sequence Listing.

MALTOOLIGOSYL TREHALOSE SYNTHASE MUTANT AND ITS APPLICATION

CROSS-REFERENCES AND RELATED APPLICATIONS

This application claims the benefit of priority to Chinese Application No. 201710822065.8, entitled "A maltooligosyl trehalose synthase mutant and its application", filed Sep. 13, 2017, which is herein incorporated by reference in its entirety.

BACKGROUND OF THE INVENTION

Field of the Invention

The present invention relates to the field of genetic engineering and enzyme engineering, and more particularly relates to a maltooligosyl trehalose synthase mutant and its application.

Description of the Related Art

Trehalose, composed of two pyran ring linked with α,α-1,1 glucose-glycoside, is a stable non-reducing disaccharide. Because of its high safety and good stability, it is widely used in medicine, food, makeup and agriculture and other fields. Since 1995, trehalose had been approved to be used as food additives in Japan, the United States and the European Union. And it had been approved as a new resource food by the China's Ministry of Health in 2005.

In 1993, the Japanese Hiratsuka Biochemical Research Institute first discovered that synergies happened between maltooligosyl trehalose synthase (MTSase) and maltooligosyl trehalose hydrolase (MTHase), and they could produce trehalose with liquefied starch as a substrate, and the industrial production of trehalose was firstly achieved. At present, companies in China have started to produce trehalose. However, compared with the imported products, there is a clear gap in the product performance and yield. More seriously, in order to meet the market demand, trehalose price is continually declined, which has brought great challenges and pressures to trehalose production. Therefor, how to improve the yield of trehalose and achieve low-cost large-scale preparation of trehalose in order to put onto the consumer's table has become a focus of the academic and industry.

At present, two methods are mainly used for the industrial production of trehalose. The first method is to use trehalose synthase to generate trehalose from the maltose substrate through the intramolecular transfer of glycosylation action, the second method is to use MTSase and MTHase to generate trehalose from the substrate liquefied starch through the synergies. And the yield of trehalose in both methods is about 80%. However, considered the production cost and cycle, the process of trehalose preparation is more simple and the cost is lower when the substrate is starch. Therefore, there are more advantageous to use the synergies of MTSase and MTHase to produce trehalose.

The enzymes used for trehalose production by double enzyme method are usually middle-temperature or low-temperature enzymes, and the trehalose conversion rate is 80% using the enzymes from *Arthrobacter* sp. Q36, 66% using the enzymes from *Arthrobacter ramosus* S34, 70.4% using the enzymes from *Brevibaterium helvolum*. The high-temperature enzymes are also used for trehalose production, and the trehalose conversion rate is 81.5% using the enzymes from *Sulfolobus solfataricus* KM1, 80.2% using the enzymes from *Sulfohus acidocaldarius* ATCC 33909. The high-temperature enzymes have advantages of high trehalose conversion rate and good thermal stability, resulting in the ability of converting starch into trehalose at high temperature and the production system is not easy to be contaminated by bacteria. However, compared with the low-temperature enzyme system, high-temperature enzyme system usually has shortcomings of lower protein expression, lower enzyme activity, which is not conducive to its industrial applications.

DETAILED DESCRIPTION

To solve the above problems, the present invention improved the enzyme activity of maltooligosyl trehalose synthase (MTSase) using gene engineering and enzyme engineering means, which created conditions for its industrial production.

The present invention provides maltooligosyl trehalose synthase mutant with improved enzyme activity, comprising one or more of the following sets of substitutions compared with the wild-type amino acid sequence of maltooligosyl trehalose synthase: 81, 263, 284, 432, 439, 583, 585, 586, 611 or 615. The enzyme activity of the mutant is increased compared with the wild-type maltooligosyl trehalose synthase.

In one embodiment of the present invention, the wild-type maltooligosyl trehalose synthase is from *Sulfolobus acidocaldarius*.

In one embodiment of the present invention, the amino acid sequence of the wild-type maltooligosyl trehalose synthase from *Sulfolobus acidocaldarius* is set forth in SEQ ID NO:1.

In one embodiment of the present invention, the amino acid sequence of the mutant comprises a substitution of glycine (Gly) at position 81 with serine (Ser) compared with the wild-type, and the obtained mutant is named as G81S.

In one embodiment of the present invention, the amino acid sequence of the mutant comprises a substitution of glutamate (Glu) at position 263 with glycine (Gly) compared with the wild-type, and the obtained mutant is named as E263G.

In one embodiment of the present invention, the amino acid sequence of the mutant comprises a substitution of phenylalanine (Phe) at position 284 with valine (Val) compared with the wild-type, and the obtained mutant is named as F284V.

In one embodiment of the present invention, the amino acid sequence of the mutant comprises a substitution of glycine (Gly) at position 432 with aspartate (Asp) compared with the wild-type, and the obtained mutant is named as G432D.

In one embodiment of the present invention, the amino acid sequence of the mutant comprises a substitution of threonine (Thr) at position 439 with alanine (Ala) compared with the wild-type, and the obtained mutant is named as T439A.

In one embodiment of the present invention, the amino acid sequence of the mutant comprises a substitution of phenylalanine (Phe) at position 583 with leucine (Leu) compared with the wild-type, and the obtained mutant is named as F583L.

In one embodiment of the present invention, the amino acid sequence of the mutant comprises a substitution of glutamine (Gln) at position 585 with arginine (Arg) compared with the wild-type, and the obtained mutant is named as Q585R.

In one embodiment of the present invention, the amino acid sequence of the mutant comprises a substitution of glycine (Gly) at position 586 with aspartate (Asp) compared with the wild-type, and the obtained mutant is named as G586D.

In one embodiment of the present invention, the amino acid sequence of the mutant comprises a substitution of isoleucine (Ile) at position 611 with threonine (Thr) compared with the wild-type, and the obtained mutant is named as I611T.

In one embodiment of the present invention, the amino acid sequence of the mutant comprises a substitution of serine (Ser) at position 615 with glycine (Gly) compared with the wild-type, and the obtained mutant is named as S615G.

In one embodiment of the present invention, compared with the wild-type, the amino acid sequence of the mutant comprises a substitution of phenylalanine (Phe) at position 284 with valine (Val) and a substitution of threonine (Thr) at position 439 with alanine (Ala), and the obtained mutant is named as F284V/T439A.

In one embodiment of the present invention, compared with the wild-type, the amino acid sequence of the mutant comprises a substitution of phenylalanine (Phe) at position 284 with valine (Val) and a substitution of glycine (Gly) at position 586 with aspartate (Asp), and the obtained mutant is named as F284V/G586D.

In one embodiment of the present invention, compared with the wild-type, the amino acid sequence of the mutant comprises a substitution of threonine (Thr) at position 439 with alanine (Ala) and a substitution of glycine (Gly) at position 586 with aspartate (Asp), and the obtained mutant is named as T439A/G586D.

In one embodiment of the present invention, compared with the wild-type, the amino acid sequence of the mutant comprises a substitution of threonine (Thr) at position 439 with alanine (Ala) and a substitution of glutamine (Gln) at position 585 with arginine (Arg), and the obtained mutant is named as T439A/Q585R.

In one embodiment of the present invention, compared with the wild-type, the amino acid sequence of the mutant comprises a substitution of glycine (Gly) at position 432 with aspartate (Asp) and a substitution of glycine (Gly) at position 586 with aspartate (Asp), and the obtained mutant is named as G432D/G586D.

In one embodiment of the present invention, compared with the wild-type, the amino acid sequence of the mutant comprises a substitution of glycine (Gly) at position 81 with serine (Ser), a substitution of phenylalanine (Phe) at position 284 with valine (Val) and a substitution of serine (Ser) at position 615 with glycine (Gly), and the obtained mutant is named as G81S/F284V/S615G.

In one embodiment of the present invention, compared with the wild-type, the amino acid sequence of the mutant comprises a substitution of phenylalanine (Phe) at position 284 with valine (Val), a substitution of threonine (Thr) at position 439 with alanine (Ala) and a substitution of glycine (Gly) at position 586 with aspartate (Asp), and the obtained mutant is named as F284V/T439A/G586D.

In one embodiment of the present invention, compared with the wild-type, the amino acid sequence of the mutant comprises a substitution of glycine (Gly) at position 81 with serine (Ser), a substitution of phenylalanine (Phe) at position 284 with valine (Val), a substitution of threonine (Thr) at position 439 with alanine (Ala) and a substitution of serine (Ser) at position 615 with glycine (Gly), and the obtained mutant is named as G81S/F284V/T439A/S615G.

In one embodiment of the present invention, compared with the wild-type, the amino acid sequence of the mutant comprises a substitution of glycine (Gly) at position 81 with serine (Ser), a substitution of phenylalanine (Phe) at position 284 with valine (Val), a substitution of glycine (Gly) at position 586 with aspartate (Asp) and a substitution of serine (Ser) at position 615 with glycine (Gly), and the obtained mutant is named as G81S/F284V/G586D/S615G.

In one embodiment of the present invention, compared with the wild-type, the amino acid sequence of the mutant comprises a substitution of glutamate (Glu) at position 263 with glycine (Gly), a substitution of phenylalanine (Phe) at position 284 with valine (Val), a substitution of phenylalanine (Phe) at position 583 with leucine (Leu), a substitution of isoleucine (Ile) at position 611 with threonine (Thr) and a substitution of serine (Ser) at position 615 with glycine (Gly), and the obtained mutant is named as E263 G/F284V/F583L/I611T/S615G.

The present invention also provides a method of preparing the maltooligosyl trehalose synthase mutant.

In one embodiment of the present invention, said method comprises the following steps:

(1) primers for site-directed mutations of the mutant are designed according to the substitution site, and a vector carrying the maltooligosyl trehalose synthase gene is used as a template for site-directed mutagenesis; a recombinant plasmid containing the gene encoding the mutant is obtained;

(2) The recombinant plasmid is transformed into a host cell;

(3) positive clones are selected and cultured with a fermentation culture; the cells are collected by centrifugation, and the cell broken supernatant is the crude enzyme solution of the maltooligosyl trehalose synthase mutant.

In one embodiment of the present invention, said vector is any one of plasmid vectors, such as pUC series, pET series, or pGEX series.

In one embodiment of the present invention, said host cell is a bacteria cell or a fungal cell.

In one embodiment of the present invention, said bacteria is gram-negative or gram-positive bacteria.

In the present, the mutant is marked as "original amino acid, position, substituted amino acids". For example, G81S indicates a substitution of Gly in position 81 with Ser. The position number corresponds to the amino acid sequence of the wild-type maltooligosyl trehalose synthase shown in SEQ ID NO:1. And F284V/T439A indicates the position of 284 and 439 are both mutated.

The present invention provides a series of maltooligosyl trehalose synthase mutants with improved enzyme activity in host. In a suitable culture conditions, the enzyme activities of mutants G81S, E263G, F284V, G432D, T439A, F583L, Q585R, G586D, I611T, S615G, F284V/T439A, F284V/G586D, G432D/G586D, T439A/Q585R, T439A/G586D, G81S/F284V/S615G, F284V/T439A/G586D, G81S/F284V/T439A/S615G, G81S/F284V/G586D/S615G, E263G/F284V/F583L/I611T/S615G are 1.2 fold, 1.1 fold, 2.1 fold, 1.2 fold, 2.1 fold, 1.2 fold, 1.1 fold, 1.4 fold, 1.19 fold, 1.17 fold, 3.1 fold, 2.4 fold, 1.6 fold, 2.4 fold, 2.7 fold, 3.2 fold, 3.4 fold, 3.8 fold, 3.6 fold, 4.0 fold of the wild-type, respectively.

EXAMPLES

Example 1: Expression of Wild-Type Maltooligosyl Trehalose Synthase treY/pET24a/BL21(DE3) stored in the glycerol tubules in laboratory was inoculated with LB liquid medium containing 100 mg·L$^{-1}$ kanamycin for 8 h, and the obtained seed was added to TB liquid fermentation medium containing 100 mg·L$^{-1}$ kanamycin by 5% inoculation amount. After incubation at 37° C. for 2 hours, IPTG (isopropylthio-β-D-galactoside) was added to a final concentration of 0.01 mmol·L$^{-1}$ and the *E. coli* was incubated at 25° C. for another 24 hours. The cells were collected by centrifugation at 4° C. and 12,000 rpm for 10 mins and then resuspended with 20 mmol·L$^{-1}$ pH 8.0 Na$_2$HPO$_4$—NaH$_2$PO$_4$ buffer and mixed. The suspension was treated with an ultrasonic cell crusher to break the cell wall, and the supernatant obtained by centrifugation at 12000 rpm for 10 mins was the intracellular crude enzyme solution.

Example 2: Preparation and Expression of the Maltooligosyl Trehalose Synthase Mutant with Single Mutation (1) Preparation of the Mutant:

primers for site-directed mutations were designed according to gene sequence of maltooligosyl trehalose synthase, and mutations were introduced into to the maltooligosyl trehalose synthase gene treY to obtain mutant G81S, E263G, F284V, G432D, T439A, F583L, Q585R, G586D, I611T and S615G. The mutant gene was verified by sequencing and the expression vector carrying the correct mutant gene was introduced into *Escherichia coli* to express the mutant maltooligosyl trehalose synthase with single site mutation.

The PCR amplification of the gene coding the target mutant was carried out by rapid PCR technique, and the expression vector treY/pET-24a(+) carrying the gene encoding the wild-type maltooligosyl trehalose synthase was used as a template.

The primers for G81S:
Forward primer: 5'-CGCATACCATTGGCCTG AGCATCATTCAG-3' (the mutant base was underlined)
Reverse primer: 5'-CTGAATGAT GCTCAGGCCAATGGTATGCG-3' (the mutant base was underlined)

The primers for E263G:
Forward primer: 5'-GGGTTTCCAGGAG GGACTGAAACTGAAC-3' (the mutant base was underlined)
Reverse primer: 5'-GTTCAGTTTCAG TCCCTCCTGGAAACCC-3' (the mutant base was underlined)

The primers for F284V:
Forward primer: 5'-CTATAGCAATCTGCTG GTTAACTTCAACCAGG-3' (the mutant base was underlined)
Reverse primer: 5'-CCTGGTTGAAGTT AACCAGCAGATTGCTATAG-3' (the mutant base was underlined)

The primers for G432D:
Forward primer: 5'-CAAAAGCGTCGT GACAAAATTACCCTGAATGC-3' (the mutant base was underlined)
Reverse primer: 5'-GCATTCAGGGTAATTTT GTCACGACGCTTTG-3' (the mutant base was underlined)

The primers for T439A:
Forward primer: 5'-CAAAATTACCCTGAATGCG GCGAGCACCCATG-3' (the mutant base was underlined)
Reverse primer: 5'-CATGGGTGCT CGCCGCATTCAGGGTAATTTTG-3' (the mutant base was underlined)

The primers for F583L:
Forward primer: 5'-CCGGTATTCCGGAC CTCTATCAAGGC-3' (the mutant base was underlined)
Reverse primer: 5'-GCCTTGATA GAGGTCCGGAATACCGG-3' (the mutant base was underlined)

The primers for Q585R:
Forward primer: 5'-CCGGACTTCTAT CGAGGCACCGAAATC-3' (the mutant base was underlined)
Reverse primer: 5'-GATTTCGGTGCC TCGATAGAAGTCCGG-3' (the mutant base was underlined)

The primers for G586D:
Forward primer: 5'-CCGGACTTCTATCAA GACACCGAAATCTGG-3' (the mutant base was underlined)
Reverse primer: 5'-CCAGATTTCGGT GTCTTGATAGAAGTCCGG-3' (the mutant base was underlined)

The primers for I611T:
Forward primer: 5'-GAAGCTGCATGAG ACCCTGGAGAAAAGC-3' (the mutant base was underlined)
Reverse primer: 5'-GCTTTTCTCCAG GGTCTCATGCAGCTTC-3' (the mutant base was underlined)

The primers for S615G:
Forward primer: 5'-CATGAGATCCTGGAGAAA GGCAAGAAGTTC-3' (the mutant base was underlined)
Reverse primer: 5'-GAACTTCTT GCCTTTCTCCAGGATCTCATG-3' (the mutant base was underlined).

The PCR reaction system of 50 µL contained 5× PS buffer 10 µL, 2.5 mmol·L$^{-1}$ dNTPs Mix 4 µL, the forward primer (10 µmol·L$^{-1}$) 1 µL, the reverse primer (10 µmol·L$^{-1}$) 1 µL, the template DNA 1 µL, PrimerStar HS (5 U·µL$^{-1}$) 0.5 µL, and water.

The amplification conditions of PCR were: 5 mins at 94° C. for pre-denaturation; followed by 30 cycles: 10 s at 98° C. for denaturation, 5 s at 55° C. for annealing, 470 s at 72° C. for extension; then 10 mins at 72° C. for extend and 4° C. for insulation. The PCR products were assayed by 1% agarose gel electrophoresis.

The verified PCR product was digested with Dpn I at 37° C. in water bath for 2 hours, and then transformed to *E. coli* JM109 competent cells. The obtained transformants were plated on LB solid culture medium containing 100 mg·L$^{-1}$ kanamycin, and cultured at 37° C. for 10~12 hours. Then, the positive clones were picked and cultured in LB liquid medium for 8~10 hours.

The correct mutant was verified by sequencing, and the recombinant plasmid containing the correct mutant was transformed into host *E. coli* BL21 (DE3) competent cells, resulting recombinant strain which could express the mutant G81S, E263G, F284V, G432D, T439A, F583L, Q585R, G586D, I611T or S615G.

(2) Expression of maltooligosyl trehalose synthase mutant with the recombinant strain The expression method was the same as example 1.

Example 3: Enzyme Activity Analysis of Maltooligosyl Trehalose Synthase

Enzyme activity is defined as the amount of enzyme required per minute to convert one micromole of glucose to non-reducing sugar.

The determination of enzyme activity was carried out as follows: (1) preheat: 1.9 mL of 0.2% maltodextrin solution (DE 9~13 pH 6.0 phosphate buffer) was added to a plug test tube, and then placed in 60° C. water bath for 10 mins; (2) reaction: 0.1 mL of diluted intracellular crude enzyme solution was added and shake evenly, 3 mL DNS was added after accurate 10 mins and oscillated evenly to terminate the reaction; the reaction system was boiled for 7 mins before cooled down; (3) measurement: distilled water was added to the above reaction system and the volume was setted to 15 mL; the absorbance was measured at 540 nm and the enzyme activity was calculated.

The values of $OD_{600\,nm}$ and enzyme activities of the wild-type maltooligosyl trehalose (WT) and the mutant after cultured in flask for 24 hours were shown in Table 1. And the amino acid sequence of the wild-type was set forth in SEQ ID NO:1.

The results showed that the enzyme activities of all mutants were higher than that of the wild-type.

TABLE 1

$OD_{600nm}$ and enzyme activity of the WT and the mutant with single site mutation

| maltooligosyl trehalose synthase | $OD_{600nm}$ | enzyme activity ($U \cdot g^{-1}$) | maltooligosyl trehalose synthase | $OD_{600nm}$ | enzyme activity ($U \cdot g^{-1}$) |
|---|---|---|---|---|---|
| WT | 14.6 | 230.8 | F583L | 14.9 | 279.4 |
| G81S | 14.8 | 267.8 | Q585R | 14.2 | 252.7 |
| E263G | 14.7 | 253.9 | G586D | 15.8 | 325.4 |
| F284V | 14.7 | 490.4 | I611T | 14.3 | 275.6 |
| G432D | 15.6 | 263.4 | S615G | 14.3 | 270.8 |
| T439A | 13.0 | 490.8 | | | |

Example 4: Preparation, Expression and Enzyme Activity Analysis of Maltooligosyl Trehalose Synthase Mutant with Double Site Mutations The recombinant plasmid expressing the correct mutant F284V, T439A or G432D constructed in Example 2 was used as template for rapid PCR technique with the primers designed in Example 2. And mutant F284V/T439A, F284V/G586D, T439A/G586D, T439A/Q585R or G432D/G586D with double site mutations was obtained. The correct mutant was verified by sequencing, and the recombinant plasmid expressing the correct mutant was transformed into *E. coli*, resulting recombinant strain which could express the mutant with double site mutations.

The values of $OD_{600\,nm}$ and enzyme activities of the wild-type maltooligosyl trehalose (WT, the amino acid sequence was set forth in SEQ ID NO:1) and the mutant with double site mutations after cultured in flask for 24 hours were shown in Table 2. The results showed that the enzyme activities of the all mutants were higher than that of the wild-type.

TABLE 2

$OD_{600nm}$ and enzyme activity of the WT and the mutant with double site mutations

| maltooligosyl trehalose synthase | $OD_{600nm}$ | enzyme activity ($U \cdot g^{-1}$) |
|---|---|---|
| WT | 14.6 | 230.8 |
| F284V/T439A | 14.3 | 716.9 |
| F284V/G586D | 14.6 | 558.0 |
| T439A/Q585R | 12.9 | 563.9 |
| T439A/G586D | 14.7 | 617.2 |
| G432D/G586D | 14.7 | 361.7 |

Example 5: Preparation, Expression and Enzyme Activity Analysis of Triple Mutant The recombinant plasmid expressing the correct mutant F284V or F284V/T439A constructed in Example 2 or Example 4 was used as template for rapid PCR technique with the primers designed in Example 2 to construct triple mutant. And mutant FG81S/F284V/S615G or F284V/T439A/G586D with three site mutations was obtained. The correct mutant was verified by sequencing, and the recombinant plasmid expressing the correct mutant was transformed into *E. coli*, resulting recombinant strain which could express the triple mutant.

The values of $OD_{600\,nm}$ and enzyme activities of the wild-type maltooligosyl trehalose (WT, the amino acid sequence was set forth in SEQ ID NO:1) and the triple mutants after cultured in flask for 24 hours were shown in Table 3. The results showed that the enzyme activities of the all mutants were higher than that of wild-type.

TABLE 3

$OD_{600nm}$ and enzyme activity of the WT and the triple mutant

| maltooligosyl trehalose synthase | $OD_{600nm}$ | enzyme activity ($U \cdot g^{-1}$) |
|---|---|---|
| WT | 14.6 | 230.8 |
| G81S/F284V/S615G | 14.4 | 748.5 |
| F284V/T439A/G586D | 13.9 | 778.3 |

Example 6: Preparation, Expression and Enzyme Activity Analysis of Mutant with Four Site Mutations The recombinant plasmid expressing the correct mutant G81S/F284V/S615G constructed in Example 5 was used as template for rapid PCR technique with the primers designed in Example 2, and mutant G81S/F284V/T439A/S615G or G81S/F284V/G586D/S615G with four site mutations was obtained. The correct mutant was verified by sequencing, and the recombinant plasmid expressing the correct mutant was transformed into *E. coli*, resulting recombinant strain which could express the mutant with four site mutations.

The values of $OD_{600\,nm}$ and enzyme activity of the wild-type maltooligosyl trehalose (WT, the amino acid sequence was set forth in SEQ ID NO:1) and the mutant with four site mutations after cultured in flask for 24 hours were shown in Table 4. The results showed that the enzyme activities of the all mutants were higher than that of wild-type.

TABLE 4

OD$_{600nm}$ and enzyme activity of the WT and
the mutant with four site mutations

| maltooligosyl trehalose synthase | OD$_{600nm}$ | enzyme activity (U · g$^{-1}$) |
|---|---|---|
| WT | 14.6 | 230.8 |
| G81S/F284V/T439A/S615G | 14.5 | 871.9 |
| G81S/F284V/G586D/S615G | 14.5 | 840.7 |

Example 7: Preparation, Expression and Enzyme Activity Analysis of Mutant with Five Site Mutations The recombinant plasmid expressing the correct mutant F284V constructed in Example 2 was used as template for rapid PCR technique with the primers designed in Example 2, and mutant E263G/F284V/F583L/I611T/S615G with five site mutations was obtained. The correct mutant was verified by sequencing, and the recombinant plasmid expressing the correct mutant was transformed into *E. coli*, resulting recombinant strain which could express the mutant with five site mutations.

The value of OD$_{600\ nm}$ and enzyme activity of the wild-type maltooligosyl trehalose (WT, the amino acid sequence was set forth in SEQ ID NO:1) and the mutant with five site mutations after cultured in flask for 24 hours were shown in Table 5. The results showed that the enzyme activity of the mutants was 4 folds of the wild-type.

TABLE 5

OD$_{600nm}$ and enzyme activity of the WT and
the mutant with five site mutations

| maltooligosyl trehalose synthase | OD$_{600nm}$ | enzyme activity (U · g$^{-1}$) |
|---|---|---|
| WT | 14.6 | 230.8 |
| E263G/F284V/F583L/I611T/S615G | 14.2 | 923.1 |

What is claimed is:

1. A maltooligosyl trehalose synthase mutant, consisting of a mutation compared with the amino acid sequence of a wild-type maltooligosyl trehalose synthase from *Sulfolobus acidocaldarius*, the mutation being selected from a group consisting of: a substitution at position 81, a substitution at position 263, a substitution at position 284, a substitution at position 432, a substitution at position 439, a substitution at position 583, a substitution at position 585, a substitution at position 586, a substitution at position 611, a substitution at position 615, and combinations thereof; wherein a parent amino acid sequence of the wild-type maltooligosyl trehalose synthase is set forth in SEQ ID NO: 1; wherein the maltooligosyl trehalose synthase mutant has enzymatic activity more than the wild-type maltooligosyl trehalose synthase.

2. The mutant of claim 1, compared with the wild-type, the amino acid sequence of said mutant comprises:
   a substitution of glycine (Gly) at position 81 with serine (Ser); or
   a substitution of glutamate (Glu) at position 263 with glycine (Gly); or
   a substitution of phenylalanine (Phe) at position 284 with valine (Val); or
   a substitution of glycine (Gly) at position 432 with aspartate (Asp); or
   a substitution of threonine (Thr) at position 439 with alanine (Ala); or
   a substitution of phenylalanine (Phe) at position 583 with leucine (Leu); or
   a substitution of glutamine (Gln) at position 585 with arginine (Arg); or
   a substitution of glycine (Gly) at position 586 with aspartate (Asp); or
   a substitution of isoleucine (Ile) at position 611 with threonine (Thr); or
   a substitution of serine (Ser) at position 615 with glycine (Gly); or
   a substitution of phenylalanine (Phe) at position 284 with valine (Val) and a substitution of threonine (Thr) at position 439 with alanine (Ala); or
   a substitution of phenylalanine (Phe) at position 284 with valine (Val) and a substitution of glycine (Gly) at position 586 with aspartate (Asp); or
   a substitution of threonine (Thr) at position 439 with alanine (Ala) and a substitution of glycine (Gly) at position 586 with aspartate (Asp); or
   a substitution of threonine (Thr) at position 439 with alanine (Ala) and a substitution of glutamine (Gln) at position 585 with arginine (Arg); or
   a substitution of glycine (Gly) at position 432 with aspartate (Asp) and a substitution of glycine (Gly) at position 586 with aspartate (Asp); or
   a substitution of glycine (Gly) at position 81 with serine (Ser), a substitution of phenylalanine (Phe) at position 284 with valine (Val) and a substitution of serine (Ser) at position 615 with glycine (Gly); or
   a substitution of phenylalanine (Phe) at position 284 with valine (Val), a substitution of threonine (Thr) at position 439 with alanine (Ala) and a substitution of glycine (Gly) at position 586 with aspartate (Asp); or
   a substitution of glycine (Gly) at position 81 with serine (Ser), a substitution of phenylalanine (Phe) at position 284 with valine (Val), a substitution of threonine (Thr) at position 439 with alanine (Ala) and a substitution of serine (Ser) at position 615 with glycine (Gly); or
   a substitution of glycine (Gly) at position 81 with serine (Ser), a substitution of phenylalanine (Phe) at position 284 with valine (Val), a substitution of glycine (Gly) at position 586 with aspartate (Asp) and a substitution of serine (Ser) at position 615 with glycine (Gly); or
   a substitution of glutamate (Glu) at position 263 with glycine (Gly), a substitution of phenylalanine (Phe) at position 284 with valine (Val), a substitution of phenylalanine (Phe) at position 583 with leucine (Leu), a substitution of isoleucine (Ile) at position 611 with threonine (Thr) and a substitution of serine (Ser) at position 615 with glycine (Gly).

3. An enzyme preparation for producing trehalose, comprising the mutant of claim 1.

* * * * *

SEQUENCE LISTING

```
<160> NUMBER OF SEQ ID NOS: 21

<210> SEQ ID NO 1
<211> LENGTH: 720
<212> TYPE: PRT
<213> ORGANISM: Artificial Sequence
<220> FEATURE:
<223> OTHER INFORMATION: Synthetic protein

<400> SEQUENCE: 1

Met Ile Ser Ala Thr Tyr Arg Leu Gln Leu Asn Lys Asn Phe Asn Phe
1               5                   10                  15

Gly Asp Val Ile Asp Asn Leu Trp Tyr Phe Lys Asp Leu Gly Val Ser
                20                  25                  30

His Leu Tyr Leu Ser Pro Val Leu Met Ala Ser Pro Gly Ser Asn His
            35                  40                  45

Gly Tyr Asp Val Ile Asp His Ser Arg Ile Asn Asp Glu Leu Gly Gly
    50                  55                  60

Glu Lys Glu Tyr Arg Arg Leu Ile Glu Thr Ala His Thr Ile Gly Leu
65                  70                  75                  80

Gly Ile Ile Gln Asp Ile Val Pro Asn His Met Ala Val Asn Ser Leu
                85                  90                  95

Asn Trp Arg Leu Met Asp Val Leu Lys Met Gly Lys Lys Ser Lys Tyr
            100                 105                 110

Tyr Thr Tyr Phe Asp Phe Phe Pro Glu Asp Asp Lys Ile Arg Leu Pro
        115                 120                 125

Ile Leu Gly Glu Asp Leu Asp Thr Val Ile Ser Lys Gly Leu Leu Lys
    130                 135                 140

Ile Val Lys Asp Gly Asp Glu Tyr Phe Leu Glu Tyr Phe Lys Trp Lys
145                 150                 155                 160

Leu Pro Leu Thr Glu Val Gly Asn Asp Ile Tyr Asp Thr Leu Gln Lys
                165                 170                 175

Gln Asn Tyr Thr Leu Met Ser Trp Lys Asn Pro Pro Ser Tyr Arg Arg
            180                 185                 190

Phe Phe Asp Val Asn Thr Leu Ile Gly Val Asn Val Glu Lys Asp His
        195                 200                 205

Val Phe Gln Glu Ser His Ser Lys Ile Leu Asp Leu Asp Val Asp Gly
    210                 215                 220
```

-continued

```
Tyr Arg Ile Asp His Ile Asp Gly Leu Tyr Asp Pro Glu Lys Tyr Ile
225                 230                 235                 240

Asn Asp Leu Arg Ser Ile Ile Lys Asn Lys Ile Ile Val Glu Lys
            245                 250                 255

Ile Leu Gly Phe Gln Glu Glu Leu Lys Leu Asn Ser Asp Gly Thr Thr
                260                 265                 270

Gly Tyr Asp Phe Leu Asn Tyr Ser Asn Leu Leu Phe Asn Phe Asn Gln
        275                 280                 285

Glu Ile Met Asp Ser Ile Tyr Glu Asn Phe Thr Ala Glu Lys Ile Ser
290                 295                 300

Ile Ser Glu Ser Ile Lys Lys Ile Lys Ala Gln Ile Ile Asp Glu Leu
305                 310                 315                 320

Phe Ser Tyr Glu Val Lys Arg Leu Ala Ser Gln Leu Gly Ile Ser Tyr
                325                 330                 335

Asp Ile Leu Arg Asp Tyr Leu Ser Cys Ile Asp Val Tyr Arg Thr Tyr
                340                 345                 350

Ala Asn Gln Ile Val Lys Glu Cys Asp Lys Thr Asn Glu Ile Glu Glu
            355                 360                 365

Ala Thr Lys Arg Asn Pro Glu Ala Tyr Thr Lys Leu Gln Gln Tyr Met
370                 375                 380

Pro Ala Val Tyr Ala Lys Ala Tyr Glu Asp Thr Phe Leu Phe Arg Tyr
385                 390                 395                 400

Asn Arg Leu Ile Ser Ile Asn Glu Val Gly Ser Asp Leu Arg Tyr Tyr
                405                 410                 415

Lys Ile Ser Pro Asp Gln Phe His Val Phe Asn Gln Lys Arg Arg Gly
                420                 425                 430

Lys Ile Thr Leu Asn Ala Thr Ser Thr His Asp Thr Lys Phe Ser Glu
                435                 440                 445

Asp Val Arg Met Lys Ile Ser Val Leu Ser Glu Phe Pro Glu Glu Trp
            450                 455                 460

Lys Asn Lys Val Glu Glu Trp His Ser Ile Ile Asn Pro Lys Val Ser
465                 470                 475                 480

Arg Asn Asp Glu Tyr Arg Tyr Tyr Gln Val Leu Val Gly Ser Phe Tyr
                485                 490                 495

Glu Gly Phe Ser Asn Asp Phe Lys Glu Arg Ile Lys Gln His Met Ile
                500                 505                 510

Lys Ser Val Arg Glu Ala Lys Ile Asn Thr Ser Trp Arg Asn Gln Asn
            515                 520                 525

Lys Glu Tyr Glu Asn Arg Val Met Glu Leu Val Glu Glu Thr Phe Thr
530                 535                 540

Asn Lys Asp Phe Ile Lys Ser Phe Met Lys Phe Glu Ser Lys Ile Arg
545                 550                 555                 560

Arg Ile Gly Met Ile Lys Ser Leu Ser Leu Val Ala Leu Lys Ile Met
                565                 570                 575

Ser Ala Gly Ile Pro Asp Phe Tyr Gln Gly Thr Glu Ile Trp Arg Tyr
                580                 585                 590

Leu Leu Thr Asp Pro Asp Asn Arg Val Pro Val Asp Phe Lys Lys Leu
            595                 600                 605

His Glu Ile Leu Glu Lys Ser Lys Lys Phe Glu Lys Asn Met Leu Glu
            610                 615                 620

Ser Met Asp Asp Gly Arg Ile Lys Met Tyr Leu Thr Tyr Lys Leu Leu
625                 630                 635                 640
```

Ser Leu Arg Lys Gln Leu Ala Glu Asp Phe Leu Lys Gly Glu Tyr Lys
        645                 650                 655

Gly Leu Asp Leu Glu Glu Gly Leu Cys Gly Phe Ile Arg Phe Asn Lys
        660                 665                 670

Ile Leu Val Ile Ile Lys Thr Lys Gly Ser Val Asn Tyr Lys Leu Lys
        675                 680                 685

Leu Glu Glu Gly Ala Ile Tyr Thr Asp Val Leu Thr Gly Glu Glu Ile
        690                 695                 700

Lys Lys Glu Val Gln Ile Asn Glu Leu Pro Arg Ile Leu Val Arg Met
705                 710                 715                 720

<210> SEQ ID NO 2
<211> LENGTH: 29
<212> TYPE: DNA
<213> ORGANISM: Artificial Sequence
<220> FEATURE:
<223> OTHER INFORMATION: Synthetic DNA

<400> SEQUENCE: 2
cgcataccat tggcctgagc atcattcag                                        29

<210> SEQ ID NO 3
<211> LENGTH: 29
<212> TYPE: DNA
<213> ORGANISM: Artificial Sequence
<220> FEATURE:
<223> OTHER INFORMATION: Synthetic DNA

<400> SEQUENCE: 3
ctgaatgatg ctcaggccaa tggtatgcg                                        29

<210> SEQ ID NO 4
<211> LENGTH: 28
<212> TYPE: DNA
<213> ORGANISM: Artificial Sequence
<220> FEATURE:
<223> OTHER INFORMATION: Synthetic DNA

<400> SEQUENCE: 4
gggtttccag gagggactga aactgaac                                         28

<210> SEQ ID NO 5
<211> LENGTH: 28
<212> TYPE: DNA
<213> ORGANISM: Artificial Sequence
<220> FEATURE:
<223> OTHER INFORMATION: Synthetic DNA

<400> SEQUENCE: 5
gttcagtttc agtccctcct ggaaaccc                                         28

<210> SEQ ID NO 6
<211> LENGTH: 32
<212> TYPE: DNA
<213> ORGANISM: Artificial Sequence
<220> FEATURE:
<223> OTHER INFORMATION: Synthetic DNA

<400> SEQUENCE: 6
ctatagcaat ctgctggtta acttcaacca gg                                    32

<210> SEQ ID NO 7
<211> LENGTH: 32
<212> TYPE: DNA

```
<213> ORGANISM: Artificial Sequence
<220> FEATURE:
<223> OTHER INFORMATION: Synthetic DNA

<400> SEQUENCE: 7
cctggttgaa gttaaccagc agattgctat ag                          32

<210> SEQ ID NO 8
<211> LENGTH: 32
<212> TYPE: DNA
<213> ORGANISM: Artificial Sequence
<220> FEATURE:
<223> OTHER INFORMATION: Synthetic DNA

<400> SEQUENCE: 8
caaaagcgtc gtgacaaaat taccctgaat gc                          32

<210> SEQ ID NO 9
<211> LENGTH: 32
<212> TYPE: DNA
<213> ORGANISM: Artificial Sequence
<220> FEATURE:
<223> OTHER INFORMATION: Synthetic DNA

<400> SEQUENCE: 9
gcattcaggg taattttgtc acgacgcttt tg                          32

<210> SEQ ID NO 10
<211> LENGTH: 32
<212> TYPE: DNA
<213> ORGANISM: Artificial Sequence
<220> FEATURE:
<223> OTHER INFORMATION: Synthetic DNA

<400> SEQUENCE: 10
caaaattacc ctgaatgcgg cgagcaccca tg                          32

<210> SEQ ID NO 11
<211> LENGTH: 32
<212> TYPE: DNA
<213> ORGANISM: Artificial Sequence
<220> FEATURE:
<223> OTHER INFORMATION: Synthetic DNA

<400> SEQUENCE: 11
catgggtgct cgccgcattc agggtaattt tg                          32

<210> SEQ ID NO 12
<211> LENGTH: 26
<212> TYPE: DNA
<213> ORGANISM: Artificial Sequence
<220> FEATURE:
<223> OTHER INFORMATION: Synthetic DNA

<400> SEQUENCE: 12
ccggtattcc ggacctctat caaggc                                 26

<210> SEQ ID NO 13
<211> LENGTH: 26
<212> TYPE: DNA
<213> ORGANISM: Artificial Sequence
<220> FEATURE:
<223> OTHER INFORMATION: Synthetic DNA

<400> SEQUENCE: 13
gccttgatag aggtccggaa taccgg                                 26
```

<210> SEQ ID NO 14
<211> LENGTH: 27
<212> TYPE: DNA
<213> ORGANISM: Artificial Sequence
<220> FEATURE:
<223> OTHER INFORMATION: Synthetic DNA

<400> SEQUENCE: 14
ccggacttct atcgaggcac cgaaatc                                27

<210> SEQ ID NO 15
<211> LENGTH: 27
<212> TYPE: DNA
<213> ORGANISM: Artificial Sequence
<220> FEATURE:
<223> OTHER INFORMATION: Synthetic DNA

<400> SEQUENCE: 15
gatttcggtg cctcgataga agtccgg                                27

<210> SEQ ID NO 16
<211> LENGTH: 30
<212> TYPE: DNA
<213> ORGANISM: Artificial Sequence
<220> FEATURE:
<223> OTHER INFORMATION: Synthetic DNA

<400> SEQUENCE: 16
ccggacttct atcaagacac cgaaatctgg                             30

<210> SEQ ID NO 17
<211> LENGTH: 30
<212> TYPE: DNA
<213> ORGANISM: Artificial Sequence
<220> FEATURE:
<223> OTHER INFORMATION: Synthetic DNA

<400> SEQUENCE: 17
ccagatttcg gtgtcttgat agaagtccgg                             30

<210> SEQ ID NO 18
<211> LENGTH: 28
<212> TYPE: DNA
<213> ORGANISM: Artificial Sequence
<220> FEATURE:
<223> OTHER INFORMATION: Synthetic DNA

<400> SEQUENCE: 18
gaagctgcat gagaccctgg agaaaagc                               28

<210> SEQ ID NO 19
<211> LENGTH: 28
<212> TYPE: DNA
<213> ORGANISM: Artificial Sequence
<220> FEATURE:
<223> OTHER INFORMATION: Synthetic DNA

<400> SEQUENCE: 19
gcttttctcc agggtctcat gcagcttc                               28

<210> SEQ ID NO 20
<211> LENGTH: 30
<212> TYPE: DNA
<213> ORGANISM: Artificial Sequence
<220> FEATURE:

<223> OTHER INFORMATION: Synthetic DNA

<400> SEQUENCE: 20
catgagatcc tggagaaagg caagaagttc               30

<210> SEQ ID NO 21
<211> LENGTH: 30
<212> TYPE: DNA
<213> ORGANISM: Artificial Sequence
<220> FEATURE:
<223> OTHER INFORMATION: Synthetic DNA

<400> SEQUENCE: 21
gaacttcttg cctttctcca ggatctcatg               30